(12) United States Patent
Hellgren et al.

(10) Patent No.: US 12,044,664 B2
(45) Date of Patent: Jul. 23, 2024

(54) METHOD FOR ADAPTING THE CONCENTRATION OF A SAMPLE GAS IN A GAS MIXTURE TO BE ANALYSED BY A GAS CHROMATOGRAPH ASSEMBLY, AND CHROMATOGRAPH ASSEMBLY THEREFORE

(71) Applicant: INFICON GmbH, Cologne (DE)

(72) Inventors: Johann Hellgren, Linköping (SE); Henrik Vennerberg, Linköping (SE); Fredrik Enquist, Linköping (SE)

(73) Assignee: INFICON GmbH, Cologne (DE)

( * ) Notice: Subject to any disclaimer, the term of this patent is extended or adjusted under 35 U.S.C. 154(b) by 267 days.

(21) Appl. No.: 17/788,254

(22) PCT Filed: Dec. 9, 2020

(86) PCT No.: PCT/EP2020/085259
§ 371 (c)(1),
(2) Date: Jun. 22, 2022

(87) PCT Pub. No.: WO2021/139953
PCT Pub. Date: Jul. 15, 2021

(65) Prior Publication Data
US 2023/0021741 A1    Jan. 26, 2023

(30) Foreign Application Priority Data
Jan. 10, 2020   (EP) ..................................... 20151114

(51) Int. Cl.
*G01N 30/74*  (2006.01)
*G01N 30/06*  (2006.01)
(Continued)

(52) U.S. Cl.
CPC ............. *G01N 30/74* (2013.01); *G01N 30/06* (2013.01); *G01N 30/38* (2013.01); *G01N 2030/025* (2013.01); *G01N 2030/385* (2013.01)

(58) Field of Classification Search
None
See application file for complete search history.

(56) References Cited

U.S. PATENT DOCUMENTS 3,668,935 A * 6/1972 Coelho .................. G01N 30/20
                                                       73/864.85
10,309,943 B2 * 6/2019 Hellgren ............ G01N 33/0062
(Continued)

FOREIGN PATENT DOCUMENTS

CN      103620400 A     3/2014
EP      3599463         1/2020

*Primary Examiner* — Andre J Allen
(74) *Attorney, Agent, or Firm* — Kirton McConkie; Whitney Blair

(57) ABSTRACT

Method for adapting the concentration of a sample gas in a gas mixture to be analysed by a gas chromatograph assembly (10), the gas chromatograph assembly (10) comprising a sample gas inlet (20) for introducing a sample gas to be analysed, a secondary gas inlet (40), a gas chromatograph infrared sensor (12), a gas chromatograph column (26), and a gas chromatograph bypass (28) parallel to the column (26), characterized by
a) introducing an amount of sample gas through the sample gas inlet (20),
b) introducing an amount of secondary gas through the secondary gas inlet (40),
c) mixing the sample gas and the secondary gas to a gas mixture and conducting the gas mixture via the gas chromatograph bypass (28),
d) circulating the gas mixture in a gas conducting loop (52) comprising the gas chromatograph bypass (28), (Continued)

Figure 1:
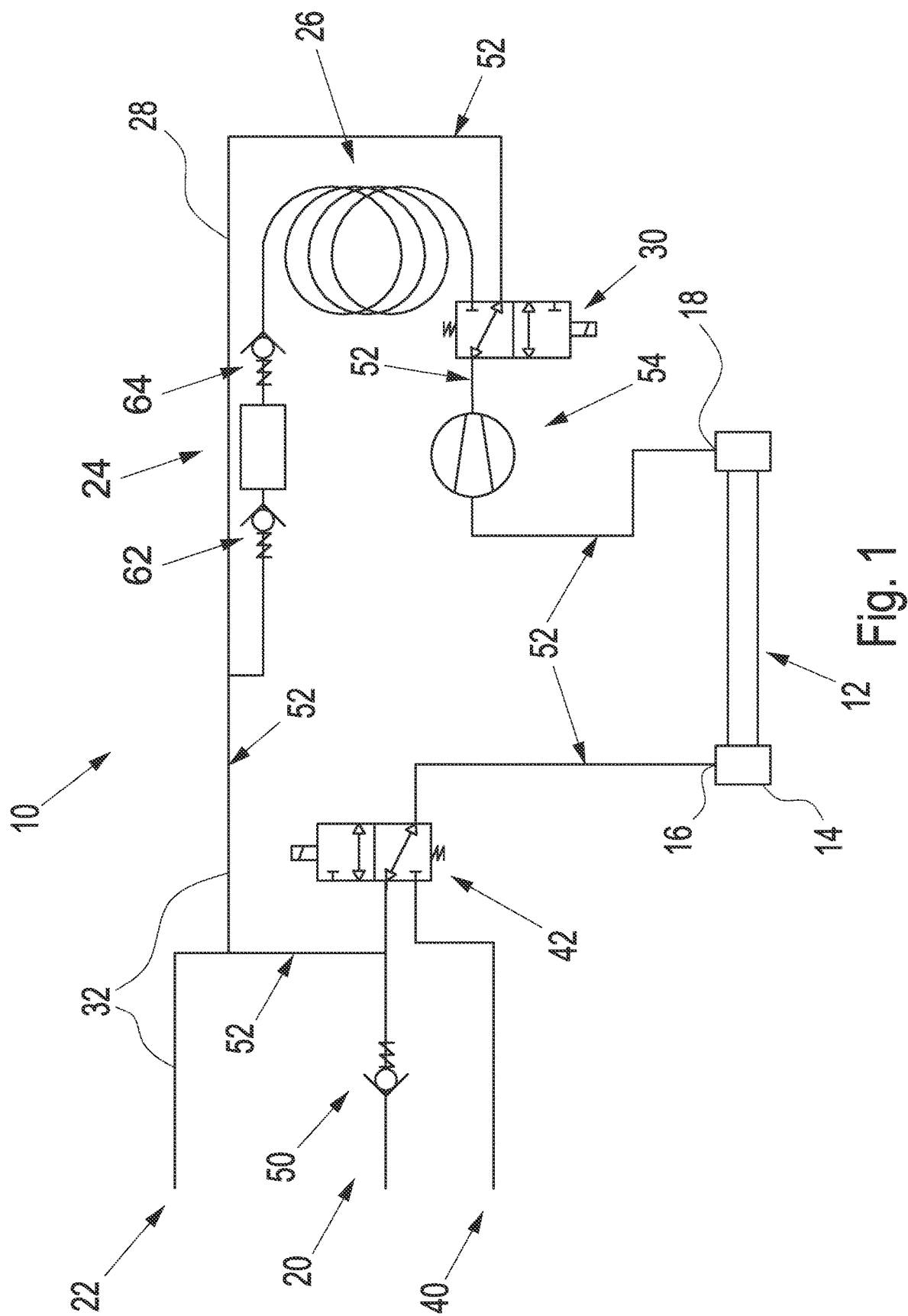

the gas chromatograph infrared sensor (12) and not comprising the gas chromatograph column (26), e) analysing the gas mixture thus obtained by means of gas chromatography employing the gas chromatograph column (26) and the gas chromatograph infrared sensor (12).

20 Claims, 7 Drawing Sheets

(51) Int. Cl.
  *G01N 30/38* (2006.01)
  *G01N 30/78* (2006.01)
  *G01N 30/02* (2006.01)

(56) References Cited

U.S. PATENT DOCUMENTS

| | | |
|---|---|---|
| 2004/0154379 A1* | 8/2004 | Enquist ............ G01M 3/226 |
| | | 73/40.7 |
| 2016/0061798 A1 | 3/2016 | Wapelhorst et al. |
| 2016/0320362 A1 | 11/2016 | Schwieters et al. |
| 2017/0012290 A1 | 5/2017 | Spartz et al. |
| 2017/0241961 A1 | 8/2017 | Kim et al. |
| 2021/0318271 A1* | 10/2021 | Hellgren ............ G01N 30/88 |

\* cited by examiner

METHOD FOR ADAPTING THE CONCENTRATION OF A SAMPLE GAS IN A GAS MIXTURE TO BE ANALYSED BY A GAS CHROMATOGRAPH ASSEMBLY, AND CHROMATOGRAPH ASSEMBLY THEREFORE

The invention concerns a method for adapting the concentration of a sample gas in a gas mixture to be analysed by a gas chromatograph assembly, as well as a gas chromatograph assembly for adapting the concentration of a sample gas to be analysed.

Gas chromatography is employed to separate gas components from a gas mixture and to detect these separated gas components. This is achieved by injecting small amounts of the gas mixture into a tube shaped column. The column is typically either a narrow capillary tube, the inner surface of which is provided with a surface active coating or a slightly larger tube filled with a surface active powder, which in both cases is called the "stationary phase". A carrier gas, such as hydrogen, helium or air is employed to carry the amount of the gas mixture to be analysed through the column. The carrier gas is usually referred to as the "mobile phase." Thus, the gas mixture to be analysed follows the mobile phase through the stationary phase, thereby pushing the gas mixture slowly through the stationary phase. Lighter components of the gas mixture travel faster, so that different gas components of the injected gas pulse leave the column at different times and can thus be detected one by one. The arrival time or travel time of the gas components is used to identify these. A gas chromatograph sensor is used in order to measure the time of arrival or travel time of each gas component. Gas chromatography is used in the forensic science, medicine and environmental protection fields.

Gas chromatography is also used in the field of gas leak detection, particularly for assessing whether a certain gas component measured on the ground surface originates from a leak in an underground pipeline carrying a natural gas. The main component of the natural gas and of gas from biological decay processes ("swamp gas") is methane. Swamp gas is produced when microorganisms digest biological waste. Before repair work for repairing a leak in a buried underground pipeline is initiated, it needs to be ensured that the gas detected at the ground surface does not originate from a swamp gas emission.

This can be achieved by means of gas chromatography. In this regard, it needs to be considered that natural gas always contains a certain amount of ethane, while swamp gas never contains any amount of ethane. Thus, if ethane is detected via gas chromatography, this is an indication that the gas detected on a ground surface does not originate from swamp gas but rather from a gas leak in an underground pipeline carrying natural gas, such as methane.

The concentration of sample gas in the gas sample analysed by the gas chromatograph is critical. On the one hand, the concentration needs to be high enough in order to achieve a sufficient measurement signal. On the other hand, the concentration must not exceed a certain value, in order to avoid overloading of the stationary phase within the gas chromatograph column. Overloading creates distorted peaks in the measurement signal and can lead to misinterpretation of the gas type, or can even result in covering or hiding peaks of several gas components. This is particularly critical for a simple column without any temperature control.

The object of the invention is to provide a method for adapting the concentration of a sample gas in a gas mixture to be analysed by a gas chromatograph assembly. A gas chromatograph assembly for adapting the concentration of a sample gas in a gas mixture to be analysed shall also be provided.

The subject matter of the invention is defined by each of independent claims 1 and 11.

The gas chromatograph assembly of the invention comprises a sample gas inlet for introducing a sample gas to be analysed, a secondary gas inlet, as well as a gas chromatograph infrared sensor, a gas chromatograph column, and a gas chromatograph bypass parallel to the column.

According to the invention,
a) an amount of sample gas is introduced into the gas chromatograph assembly through the sample gas inlet,
b) an amount of secondary gas is introduced through the secondary gas inlet,
c) the sample gas and the secondary gas are mixed to a gas mixture which is conducted via the gas chromatograph bypass,
d) circulating the gas mixture in a gas conducting loop comprising the gas chromatograph bypass and the gas chromatograph infrared sensor and not comprising the gas chromatograph column.
e) The gas mixture thus obtained is analysed by means of gas chromatography employing the gas chromatograph column and the gas chromatograph sensor.

In other words, a gas mixture is created from the sample gas which enters through the sample gas inlet, and from the secondary gas which enters through the secondary gas inlet. The gas mixture is conducted via the gas chromatograph bypass, such that the gas mixture can actually flow within the gas chromatograph assembly without being blocked by the column. The gas chromatograph bypass facilitates the mixing of the two gas components.

An important aspect of the invention is that the gas chromatograph sensor is an infrared sensor, preferably a wide range IR sensor, such as an infrared absorption cuvette. A separate secondary infrared sensor is than not necessary, in order to combine the advantages of a gas chromatograph sensor and a secondary infrared sensor assembly.

The invention may achieve a gradual reduction of the concentration of sample gas within the gas mixture by repeating the introduction of the secondary gas and the mixing of the newly introduced secondary gas with the gas mixture already present within the gas chromatograph assembly without further introducing sample gas. The reduction of the sample gas concentration may be performed until the concentration of sample gas within the gas mixture reaches a desired predetermined level, at which a sufficient measurement signal from the gas chromatograph sensor is generated without overloading of the stationary phase in the column.

The mixing of sample gas and secondary gas for obtaining a gradual reduction of the sample gas concentration may be obtained via a ratiometric continuous mixing, such as via two flow regulators setting a suitable ratio of sample gas and secondary gas. One of these two flow regulators is connected to the secondary gas inlet, while the other of the two flow regulators is connected to the sample gas inlet. The ratiometric continuous mixing may be achieved with the above described gas modulation valve, or with the above mentioned two flow regulators as an alternative to a gas modulation valve. The ratiometric continued mixing is achieved by a specific ratio of introduced sample gas and introduced secondary gas, such that the gas mixture of sample gas and secondary gas comprises an amount of sample gas and an amount of secondary gas corresponding to the specific ratio.

The sample gas concentration is preferably measured during or before step d), i.e. before the introduction of sample gas or secondary gas is repeated, in order to determine whether the sample gas concentration has already reached the predetermined level. This measurement can be made with the infrared sensor.

As an alternative to the sample gas concentration measurement during or before step d), steps b), c) and d) may be repeated without step a) a predetermined number of times without measuring the sample gas concentration.

The gas chromatograph assembly comprises a gas conducting loop comprising the gas chromatograph bypass and the gas chromatograph sensor, but not the gas chromatograph column in order to achieve mixing of the sample gas and the secondary gas during circulation through the loop. In the case that the loop also comprises a secondary sensor assembly, the sample gas concentration can be measured at every cycle, or even continuously, in order to be able to measure and control the gradual increase or decrease of the sample gas concentration.

The loop may comprise a gas modulation valve being adapted to alternatingly connect either of the sample gas inlet and the secondary gas inlet with the loop. In this example, the secondary gas inlet can be a reference gas inlet which is usually employed to compare the gas sample with a reference gas. In particular, the gas modulation valve may connect the sample gas inlet with the loop during step a) while separating the secondary/reference gas inlet from the loop. Likewise, during step b) the gas modulation valve connects the secondary gas inlet with the loop while separating the sample gas inlet from the loop.

In a typical embodiment, the gas modulation valve connects the sample gas inlet and the secondary/reference gas inlet with the gas chromatograph infrared sensor assembly.

The gas chromatograph infrared sensor assembly comprises a sensor inlet at a first end of the infrared sensor, and a sensor outlet at a second end of the infrared sensor. During step a), the sensor inlet may be connected to the sample gas inlet, while the reference gas inlet is separated from the sensor inlet. Gas is then drawn from the sample gas inlet through the infrared sensor, and conducted to the gas chromatograph sensor via the gas chromatograph bypass. Likewise, in step b), the sensor inlet may be connected to the reference gas inlet, while separating the sample gas inlet from the sensor inlet. Gas is then drawn from the reference gas inlet through the infrared sensor.

The gas mixture of the sample gas and the secondary gas (reference gas) may be circulated through a gas conducting loop comprising the gas chromatograph sensor bypass, the gas chromatograph infrared sensor, the gas modulation valve and a gas chromatograph valve.

The gas chromatograph valve can be a switching valve adapted to switch between the gas chromatograph column and the gas chromatograph bypass to conduct gas either through the gas chromatograph column or through the gas chromatograph bypass into the gas chromatograph infrared sensor.

Preferably, during step c), both the sample gas inlet and the secondary inlet are separated from the loop. In particular, the secondary sensor assembly inlet may be separated from the reference gas inlet while still separating the sample gas inlet from the sensor inlet.

In general, it is preferred that the gas mixture is allowed to circulate in the loop for some time to mix the secondary gas and the sample gas. In particular, the secondary gas may be air. In order to achieve this, the secondary inlet may be an inlet from open atmosphere, i.e. an inlet being open to atmosphere.

A predetermined amount of the gas mixture may be injected into the gas chromatograph column by opening the gas chromatograph valve for a predetermined amount of time. After the gas chromatograph valve is closed, the gas chromatograph sensor/sensors may be purged by drawing air from either the sample gas inlet or the secondary/reference gas inlet, and conducting said air to the gas chromatograph infrared sensor via the gas chromatograph bypass. Thereafter, the gas chromatograph valve may be opened and air can be drawn or pushed through the gas chromatograph column into the gas chromatograph sensor for analysing the gas mixture by means of gas chromatography.

In general, the invention allows to dilute the sample gas in repeated cycles, i.e. gradually, in a controlled manner. After measuring the sample gas concentration, the entire system may first be purged, and then the gas modulation valve may be used to draw a number of short pulses from the sample gas inlet and thereby inject sample gas in the stream of gas mixture, or air stream drawn from the secondary inlet. The stream of sample gas and secondary gas is then allowed to circulate in the loop for mixing before injecting a small amount of the obtained gas mixture into the gas chromatograph column.

Figure 2:
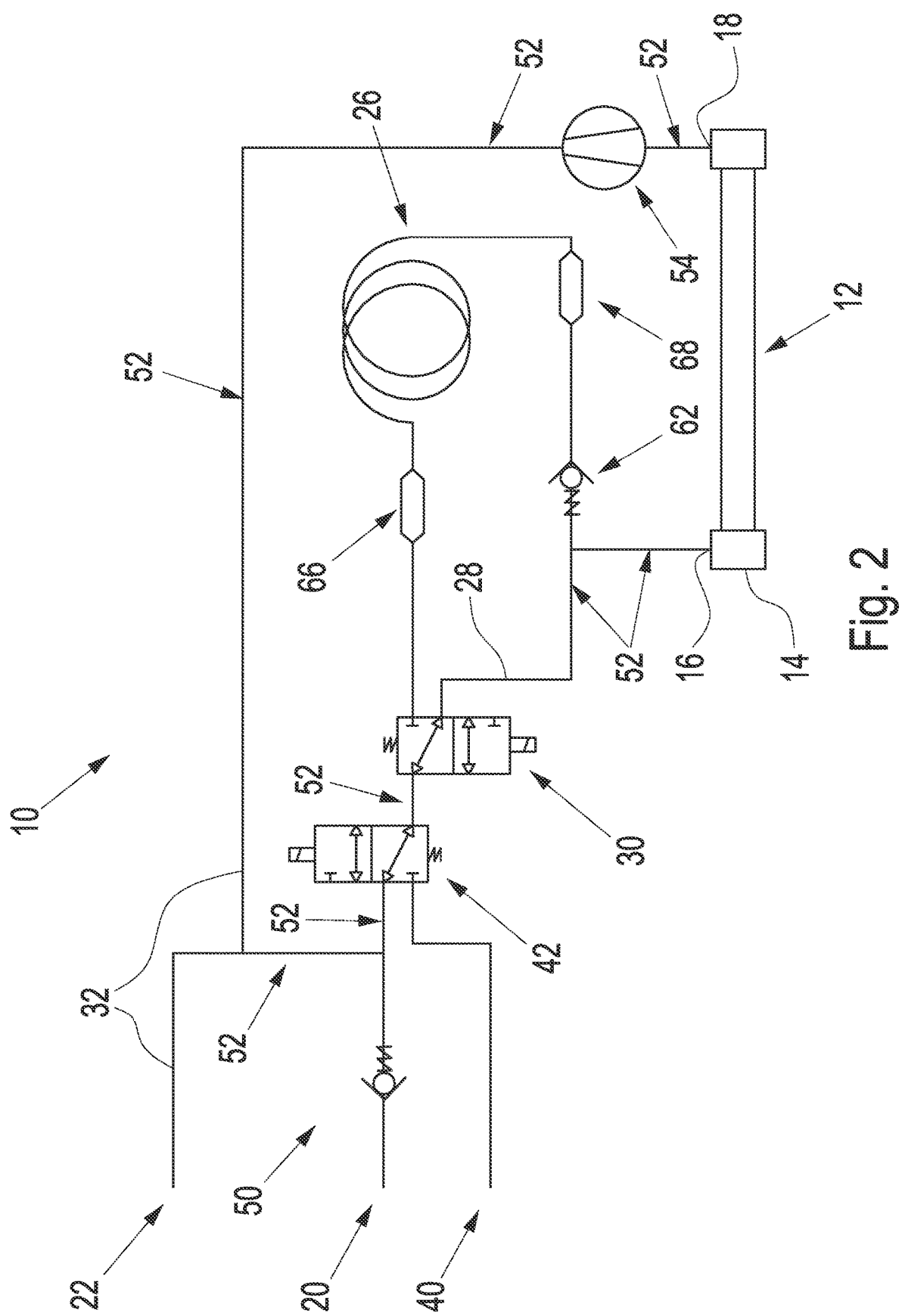
Figure 3:
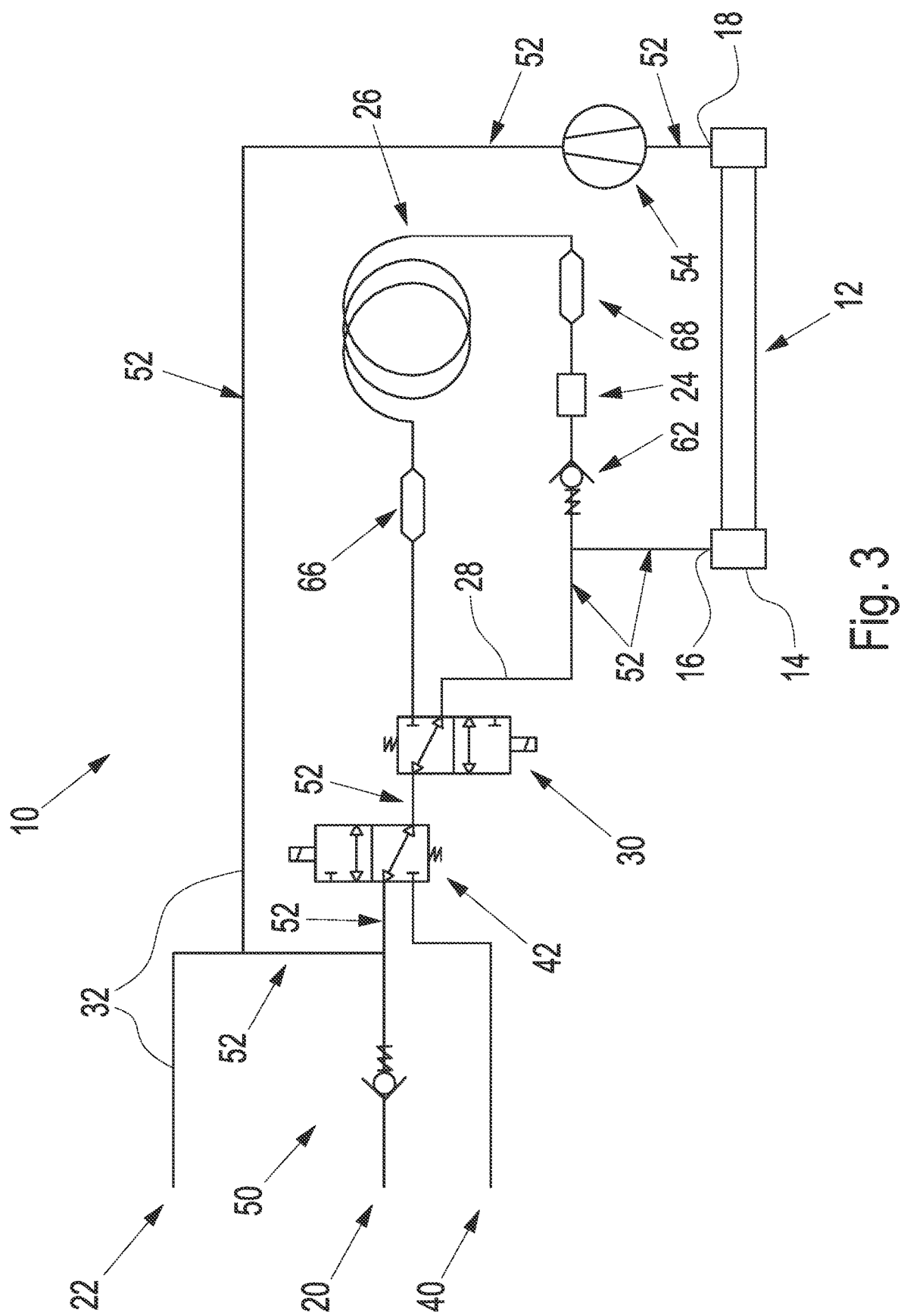
Figure 4:
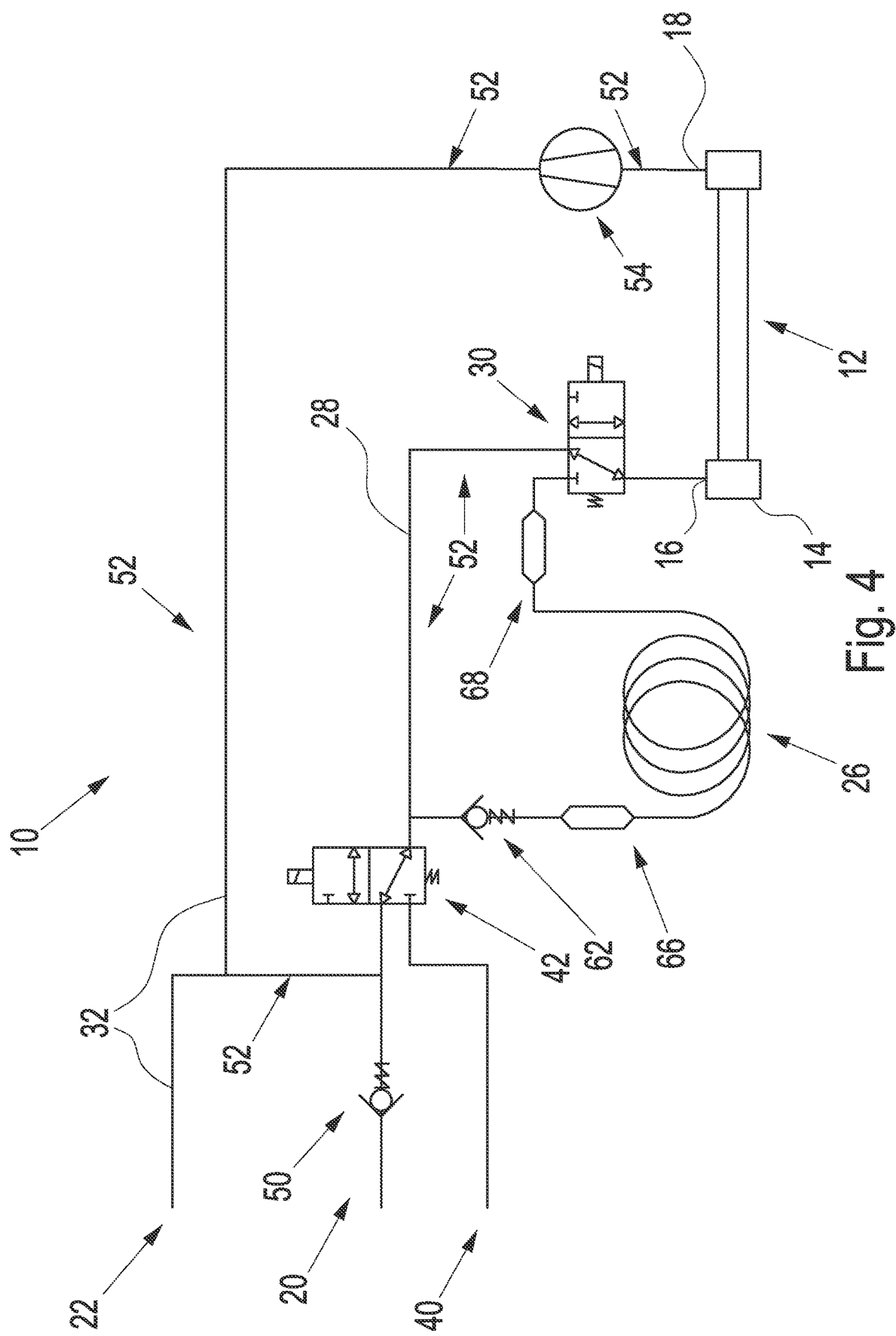
Figure 5:
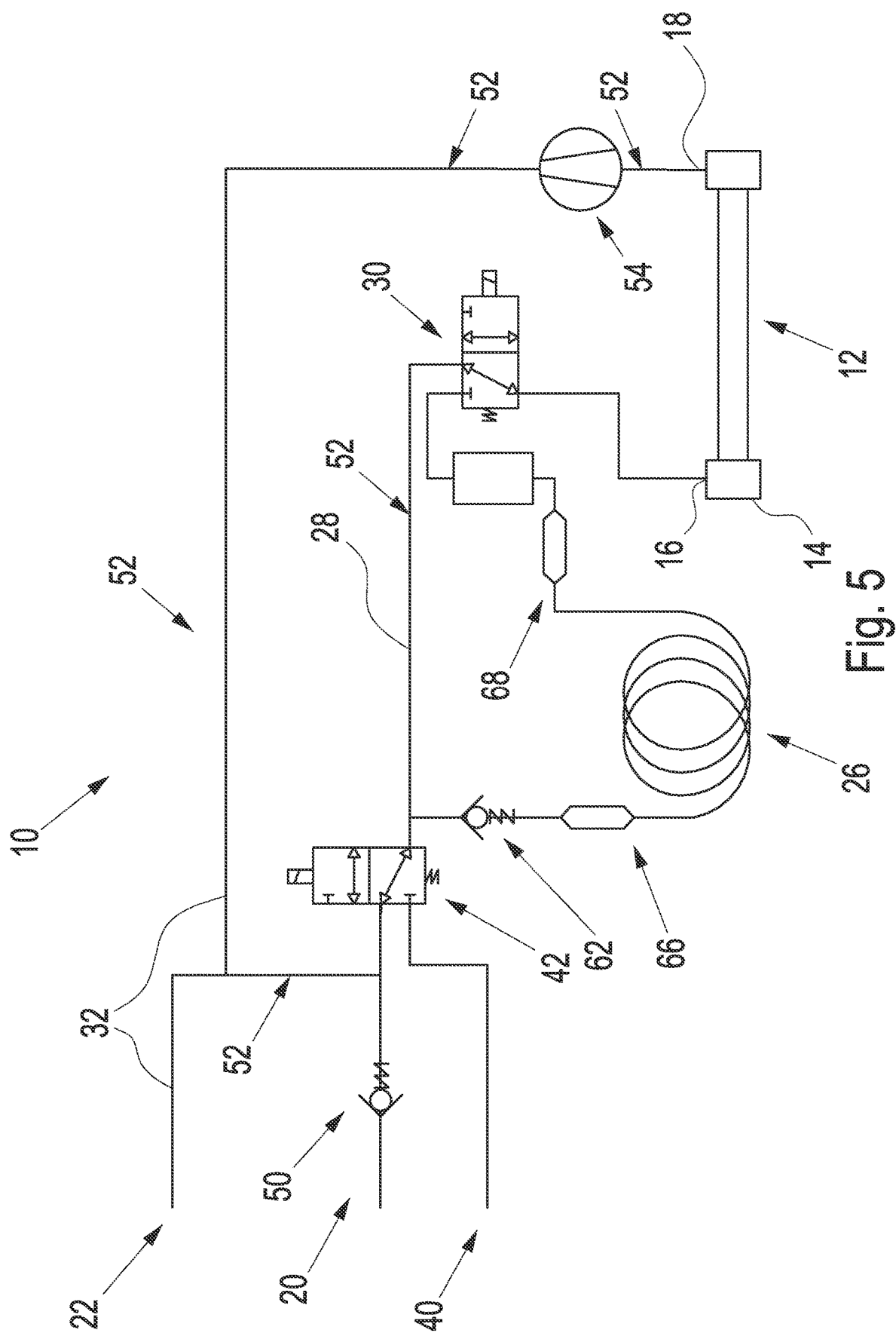
Figure 6:
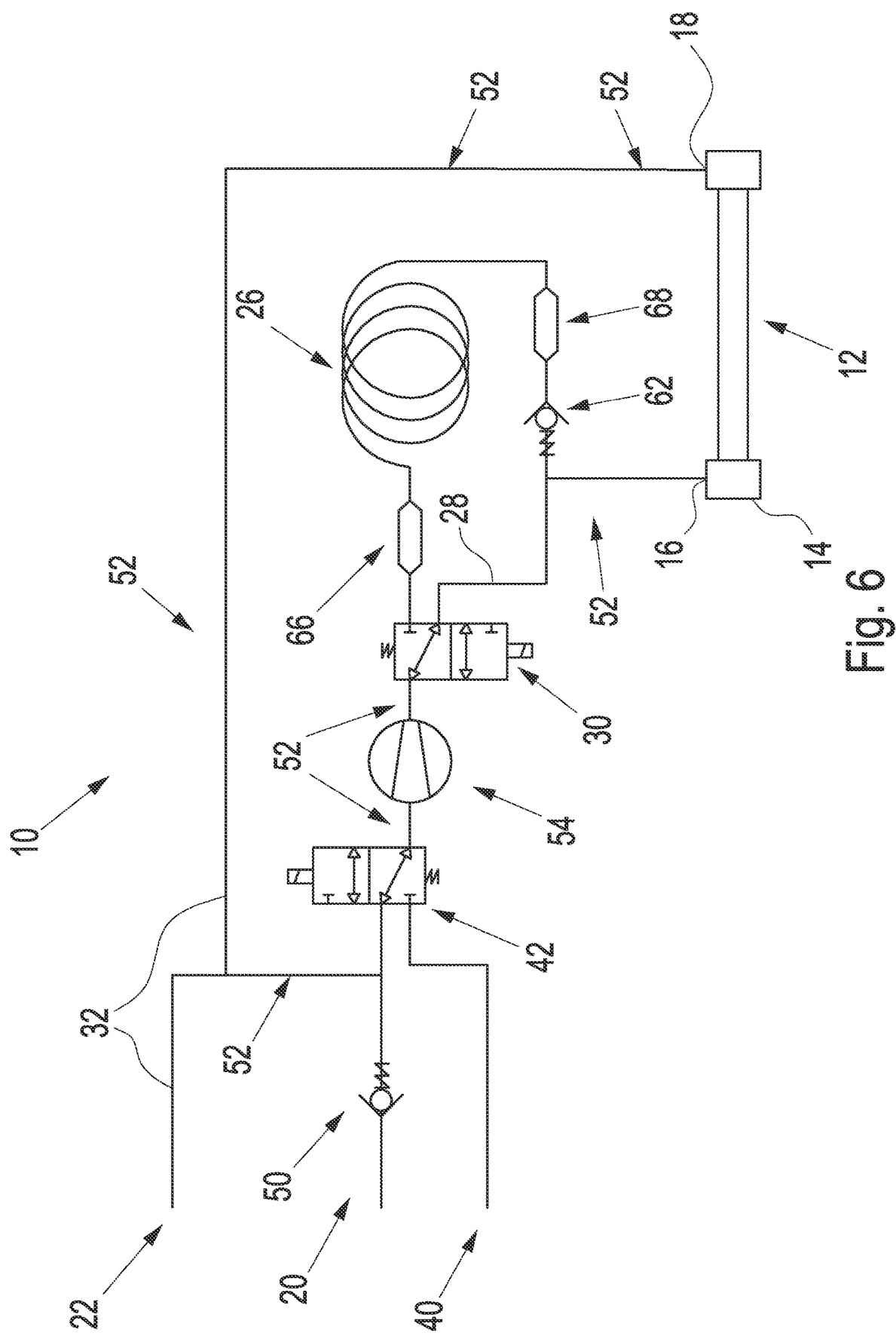
Figure 7:
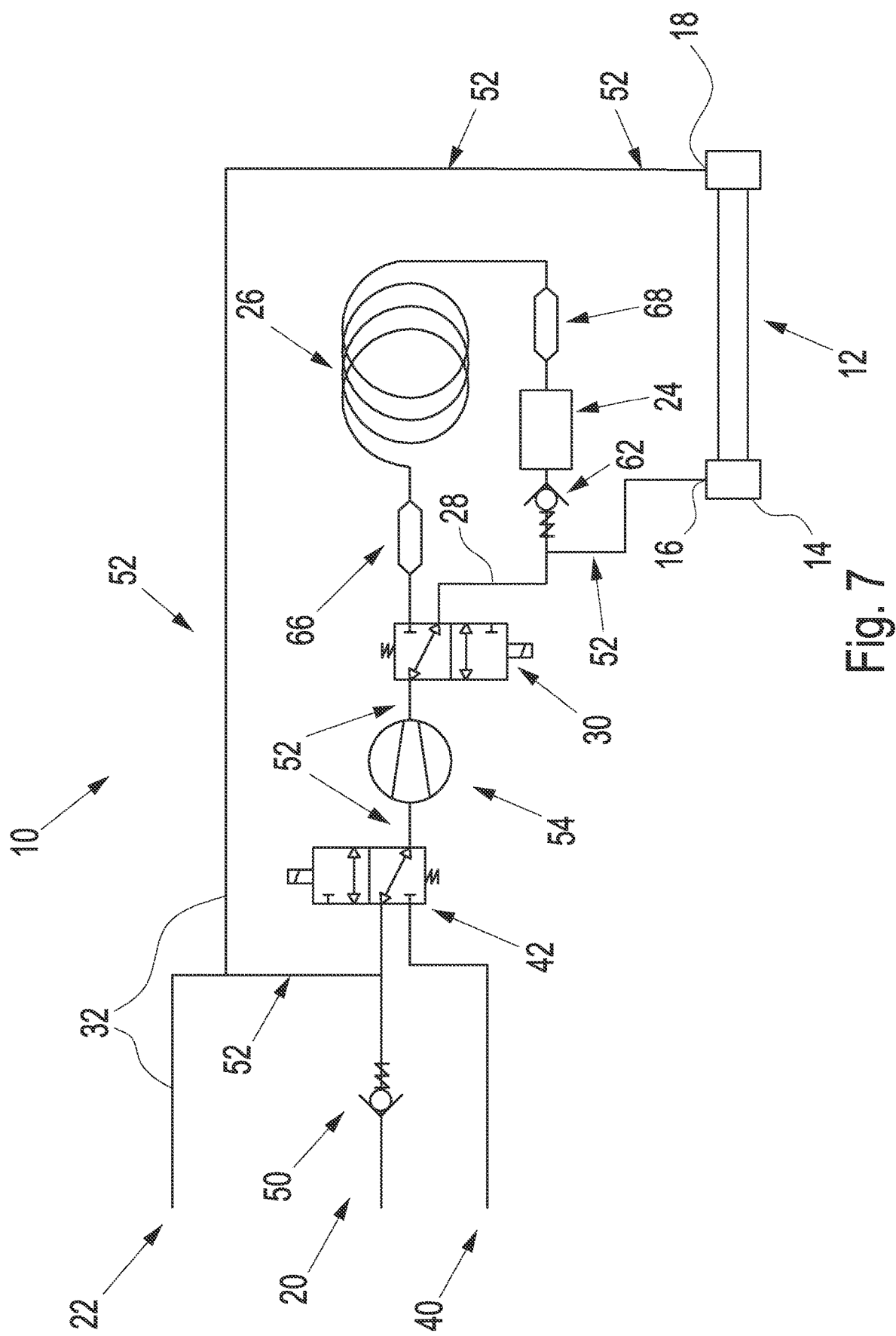

In the following, exemplary embodiments of the invention will be explained with reference to the figures. In particular, FIG. 1 shows the general layout of a first embodiment,
FIG. 2 shows a general layout of a second embodiment,
FIG. 3 shows a general layout of a third embodiment,
FIG. 4 shows a general layout of a fourth embodiment,
FIG. 5 shows a general layout of a fifth embodiment,
FIG. 6 shows a general layout of a sixth embodiment and
FIG. 7 shows a general layout of a seventh embodiment.

All figures show a gas chromatograph assembly 10 comprising a sample gas inlet 20 for introducing a sample gas to be analysed, a secondary gas inlet 40, being a reference gas inlet which is open to atmosphere. The gas chromatograph assembly 10 further comprises a gas chromatograph infrared sensor 12, a gas chromatograph column 26, and a gas chromatograph bypass 28 parallel to the column 26.

A gas chromatograph valve 30 is provided, being adapted to switch between the gas chromatograph column 26 and the gas chromatograph bypass 28 to conduct gas either through the gas chromatograph column 26 or the gas chromatograph bypass 28 into the gas chromatograph infrared sensor 12.

A secondary sensor 24 in the form of a solid state sensor, flammable gas sensor, pellistor or metal oxide sensor (MOS) is provided for measurement of the sample gas concentration.

The gas chromatograph infrared sensor 12 comprises a sensor inlet 16 at a first end, and a sensor outlet 18 at a second end of the gas chromatograph infrared sensor 12.

The sample gas inlet 20 and the secondary gas inlet 40 are connected in parallel to a gas modulation valve 42, which is adapted to alternatingly connect either of the sample gas inlet 20 and the secondary gas inlet 40 to the secondary sensor assembly 12. The sample gas inlet 20 is connected to the gas modulation valve 42 via a check valve 50.

The gas chromatograph sensor 12 is connected to an exhaust outlet 22 via an exhaust line 32. The exhaust line 32 is connected to the gas flow path connecting the sample gas inlet 20 and the gas modulation valve 42, thereby forming a loop 52. In particular, the loop 52 comprises the gas modulation valve 42, the gas chromatograph valve 30, an additional gas pump 54 in the gas flow path connecting the sensor outlet 18 and the exhaust line 32. Alternatively, the exhaust line 32 and the loop 52 may be connected to respective separate outlets of the sensor 12.

The loop 52 is adapted to circulate the gas mixture of the sample gas and of the secondary gas a number of times before measuring the sample gas concentration with the gas sensor 12. Once the sample gas concentration is sufficiently reduced, the gas chromatograph valve 30 switches from the gas chromatograph bypass 28 to the gas chromatograph column 26 for a predetermined amount of time in order to inject a short gas pulse of the gas mixture into the column 26.

In all embodiments, the gas chromatograph valve 30 switches between the column 26 and the bypass 28. In the embodiment of FIG. 1, the gas chromatograph valve 30, the column 26 and the bypass 28 are comprised in the gas flow path connecting the sensor outlet 18 with the exhaust line 32. This gas flow path also comprises the additional gas pump 54.

In the embodiment according to FIG. 2, the gas chromatograph valve 30, the column 26 and the bypass 28 are comprised in the gas flow path connecting the gas modulation valve 42 and the sensor inlet 16.

In FIG. 1, element 62 is a non-return valve/check valve suitably described as "means" for preventing gas transfer from loop into GC sensor and column.

Element 64 is preventing sample gas remaining in the column 26 to reach the sensor 24 when the device is in standby. Sample gas leaking in that way could otherwise be trapped around the GC sensor 12 without escape route. Build up such remaining gases could overload the GC sensor 12.

One embodiment is described by FIG. 2. We have added small volumes upstream 66 and downstream 68 of the GC column 26. These volumes 66, 68 serve the purpose of preserving the pressure difference over the column 26 so that the propagation of the gas through the GC column 26 can continue, for some time, even when the valve is closed. It will also increase the volume of gas from the GC that the pump can drag in each period of the switching. When gas modulation is used the gas in the IR cuvette 12 has to be exchanged in each period of the switching. And the volume of gas from the column 26 is an important parameter when designing using the IR sensor as the GC sensor. Further, the volumes will filter out pressure oscillations caused by the pump 54. The pump has oscillations due to its construction but the pump is also operated in a pulsed mode to lower the effective flow. The pressure downstream of the column 26 will drop when the pump 24 is on due to the resistance in the column and then the pressure will approach atmosphere again when the pump is off. The volumes will dampen this.

The upstream volume 66 pushes air through the column to "refill" the downstream volume 68 when pump is off.

This is important as the pressure oscillations can add noise to the signal. Especially so if the oscillation are close to or equal to the modulation frequency of the valve.

The FIG. 2 placement of the column 26 has some risk that sample gas or air (when loop 52 is fully purged) can leak in through non-return valve 62 in to the input end of the column 26.

This could cause two problems:
Issue A) Sample gas pushed in increases the injected volume and thereby affecting accuracy of quantification of the different gas peaks
Issue B) Air or sample gas leaking in will delay the peaks and this may cause misinterpretation of the different gas species as this is based on eluation time.

Issues A and B can occur on their own or combined.

A variant of the FIG. 2 embodiment is shown in FIG. 3. Here is added a further separate GC sensor 24 in the form of a solid state sensor, flammable gas sensor, pellistor or metal oxide sensor, making the IR sensor 12 secondary.

Another embodiment of the IR solution is described in FIG. 4.

The difference from FIG. 2 is that the column 26 is placed between the two valves 30, 42 instead of after the GC valve 30.

The advantage of this solution is that a possible leak in the non-return valve 62 will result in some sample gas seeping in to the output end of the GC column 26. Gas in that end will pass the sensor 12 quickly when carrier gas starts pushing through the column 26. By coming out first it easy to disregard this gas as it comes before the first part of the sample fed through the column 26.

In the embodiment of FIG. 2 sample gas leaking through 62 will end up in the input end. This will not affect the quantification (issue A above) but could still affect eluate timing (issue B above).

Carrier gas is typically air and in GC context the carrier gas called "mobile phase".

A variant of the FIG. 4 embodiment is shown in FIG. 5. Here is added a separate further GC sensor 24 in the form of a solid state sensor, flammable gas sensor, pellistor or metal oxide sensor, making the IR sensor 12 secondary.

Volumes 66, 68 may be buffer volumes in the form of containers having an inlet and an outlet at opposing ends of the container and connected to the gas conducting lines. The diameter or internal dimensions of the containers are larger than the diameter of the gas conducting line.

The invention claimed is:

1. Method for adapting the concentration of a sample gas in a gas mixture to be analysed by a gas chromatograph assembly, the gas chromatograph assembly comprising
   a sample gas inlet for introducing a sample gas to be analysed,
   a secondary gas inlet,
   a gas chromatograph infrared sensor, a gas chromatograph column, and a gas chromatograph bypass parallel to the column,
characterized by
a) introducing an amount of sample gas through the sample gas inlet,
b) introducing an amount of secondary gas through the secondary gas inlet,
c) mixing the sample gas and the secondary gas to a gas mixture and conducting the gas mixture via the gas chromatograph bypass,
d) circulating the gas mixture in a gas conducting loop comprising the gas chromatograph bypass, the gas chromatograph infrared sensor and not comprising the gas chromatograph column,
e) analysing the gas mixture thus obtained by means of gas chromatography employing the gas chromatograph column and the gas chromatograph infrared sensor.

2. The method according to claim 1, wherein the sample gas concentration is measured during or before step d) to determine whether the sample gas concentration has reached the predetermined level.

3. The method according to claim 2, wherein the measuring of the sample gas concentration during or before step d) is performed with a secondary sensor.

4. The method according to claim 3, wherein during step a) the sample gas from the sample gas inlet is conducted through the secondary sensor and to the gas chromatograph infrared sensor.

5. The method according to claim 3, wherein the loop further comprises the secondary sensor.

6. The method according to claim 1, wherein the circulating according to step d) is repeated a predetermined number of times without measuring the sample gas concentration.

7. The method according to claim 1, wherein the loop comprises a gas modulation valve adapted to alternatingly connect either of the sample gas inlet and the secondary gas inlet with the loop.

8. The method according to claim 7, wherein during step a) the gas modulation valve connects the sample gas inlet with the loop while separating the secondary inlet from the loop.

9. The method according to claim 7, wherein during step b) the gas modulation valve connects the secondary gas inlet with the loop while separating the sample gas inlet from the loop.

10. The method according to claim 1, wherein during step c) both the sample gas inlet and the secondary inlet are separated from the loop.

11. Gas chromatograph assembly for adapting the concentration of a sample gas in a gas mixture to be analysed according to the method of claim 1, comprising
- a sample gas inlet for introducing a sample gas to be analysed,
- a secondary gas inlet,
- a gas chromatograph infrared sensor, a gas chromatograph column, and a gas chromatograph bypass arranged parallel to the column for bypassing the same, and
- a gas conducting loop comprising the gas chromatograph bypass and not comprising the gas chromatograph column.

12. The gas chromatograph assembly of claim 11, further comprising a secondary sensor, for measuring the sample gas concentration during or before step d).

13. The gas chromatograph assembly of claim 11, wherein the loop comprises a gas modulation valve adapted to alternatingly connect either of the sample gas inlet and the secondary gas inlet with the loop.

14. The gas chromatograph assembly according to claim 11, wherein the loop comprises a gas chromatograph valve adapted to switch between the gas chromatograph column and the gas chromatograph bypass to conduct gas either through the gas chromatograph column or the gas chromatograph bypass into the gas chromatograph infrared sensor.

15. The assembly according to claim 11, wherein the gas chromatograph infrared sensor is connected in series to the gas chromatograph column and in parallel to the gas chromatograph bypass.

16. The assembly according to claim 11, wherein the gas chromatograph column is connected in series to an upstream buffer volume and/or to a downstream buffer volume.

17. The assembly according to claim 11, wherein gas transfer from the gas conducting loop into the sensor and the gas chromatograph column is prevented, preferably by a first valve.

18. The assembly according to claim 11, wherein gas remaining in the gas chromatograph column is prevented from reaching the sensor when the assembly is in stand-by, preferably by a second valve.

19. Method according to claim 1, wherein steps b), c) and d) are repeated without step a) to gradually reduce the concentration of sample gas within the gas mixture until the concentration of sample gas within the gas mixture reaches a desired predetermined level.

20. Method according to claim 1, wherein steps a), b) and c) are performed in the form of ratiometric continued mixing by a specific ratio of introduced amount of sample gas and introduced amount of secondary gas.

* * * * *